United States Patent [19]

Brouwer et al.

[11] Patent Number: 4,684,251
[45] Date of Patent: Aug. 4, 1987

[54] SPECTROMETER

[75] Inventors: Geert Brouwer, Waalre; Sipke Wadman, Eindhoven, both of Netherlands

[73] Assignee: U.S. Philips Corporation, New York, N.Y.

[21] Appl. No.: 839,474

[22] Filed: Mar. 14, 1986

[30] Foreign Application Priority Data

Mar. 22, 1985 [GB] United Kingdom ................. 8507521

[51] Int. Cl.⁴ ............................................ G01N 21/72
[52] U.S. Cl. ..................... 356/315; 356/417
[58] Field of Search ................................ 356/315, 417

[56] References Cited

U.S. PATENT DOCUMENTS 3,644,743 2/1972 Binek et al. ......................... 356/315
4,314,764 2/1982 Liddell et al. ...................... 356/315

FOREIGN PATENT DOCUMENTS 116282 9/1979 Japan ................................ 356/315
27246 2/1984 Japan ................................ 356/315

Primary Examiner—F. L. Evans
Attorney, Agent, or Firm—Paul R. Miller

[57] ABSTRACT

A spectrometer includign a flame atomiser (7) is provided with a sample diluter comprising a mixing vessel (1) having a diluent supply channel (20) and a sample supply tube (10). The mixing vessel (1) has a converging lower portion (2) to which a outlet tube (5) is connected, the outlet tube feeding a mixture of sample and diluent to a nebuliser (47). The sample supply tube (10) is aligned with and spaced from the outlet tube (5). Sample liquid from the sample supply tube (10) passes into the outlet tube (5) as a central core (29) entrained in a sheath of diluent. The sample and diluent flow through the tube (5) with a laminar flow due to the profile of the mixing vessel (1) thus preventing the sample liquid from coming into contact with the wall of the outlet tube (5). Consequently memory effects are reduced.

The rate of flow of sample may be controlled automatically by means of a processing and control circuit (40) which has an output (B) which controls the speed of a stepping motor (61) which is arranged to advance a plunger (13) in a syringe (15) containing the sample liquid. The processing and control circuit calculates the absorption or emission of the sample in the atomiser (7) and controls the stepping motor (61) to bring the calculated value within the most sensitive range of the instrument.

6 Claims, 4 Drawing Figures

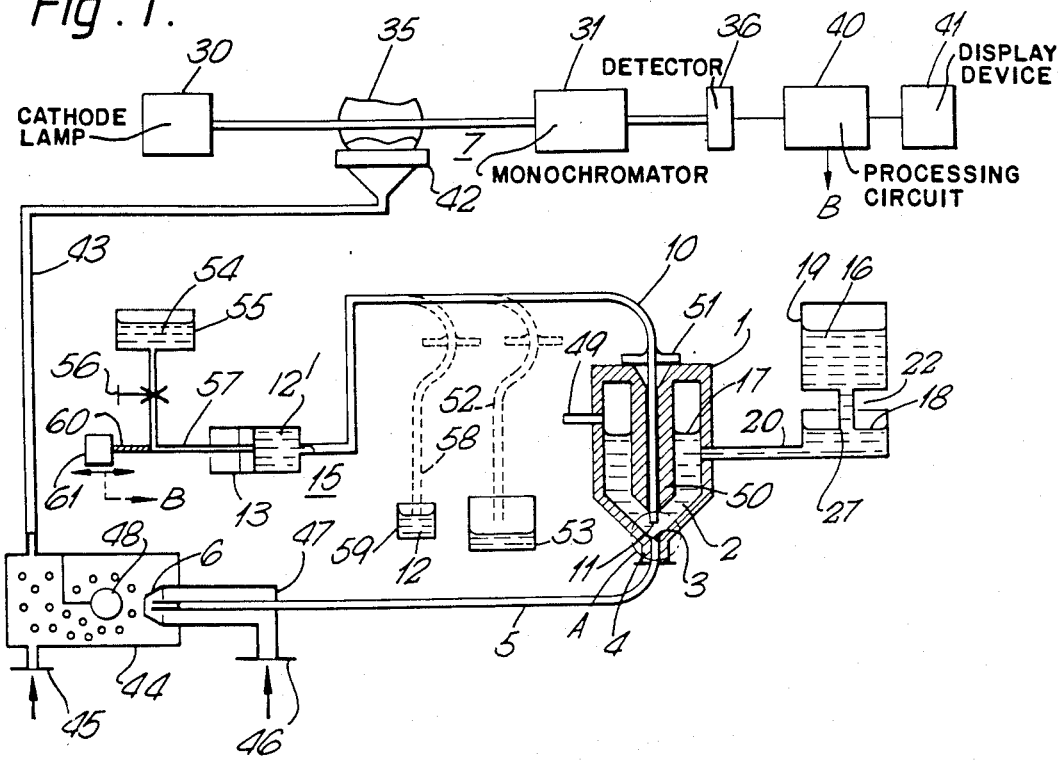

SPECTROMETER

The invention relates to aspectrometer comprising a flame atomizer in the form of a burner, a nebuliser for feeding a sample for analysis entrained in a flow of gas to the burner, a tube for feeding the sample and a diluent to the nebuliser, and means for varying the rate of flow of the sample into the tube while maintaining the total flow of sample and diluent constant.

European Patent Application No. 0118815 shows such an atomic absorbtion spectrometer. This application shows an arrangement where a single tube feeds a mixture of the sample and diluent to a nebuliser. The arrangement includes a pump in the single tube to provide a constant flow of sample and diluent mixture to the nebuliser. The diluent and sample are fed by two separate tubes to the input of the pump, the sample tube including a further pump which is controllable by the output of the spectrometer to adjust the quantity of sample fed to the nebuliser. With this arrangement the mixed sample and diluent is fed along the tube to the nebuliser and some of the sample may become attached to the walls of the tube causing a carry over of sample from one measurement to the next.

It is an object of the invention to provide a dilution system for a sample in an atomic absorbtion spectrometer in which sample carry over is reduced.

The invention provides a spectrometer as set forth in the opening paragraph characterized by delivery means for causing the sample and diluent to pass through the tube with laminar flow, the sample being entrained as a central core within the flow of diluent.

By causing the sample to be entrained as a central core within the flow of diluent contact of the sample with the walls of the tube is avoided. The sample and diluent get thoroughly mixed in the nebuliser where memory effects are not significant due to the flow of oxidant and fuel gases scavenging the nebulised sample. Thus by avoiding contact of the sample with the walls of the tube feeding the nebuliser memory effects are significantly reduced.

It should be noted that U.S. Pat. No. 3,649,829 discloses an arrangement where a sample fluid containing, for example, radio-active material is made to flow as an integral core within a column of inert fluid through a sensitive zone of a monitor, such as a radiation detector. The inert fluid acts as a sheath to prevent contamination of stationary surfaces within the sensitive zone. Sample fluid is injected into the flow of inert gas with the minimum of turbulence and mixing. However, it should also be noted that this patent specification gives no indication that such an arrangement could be used for diluting a sample with a diluent fluid and also states that integral cores of sample fluid having diameters between 0.2 and 1.5 cm have been obtained by using different cell dimensions. Thus this specification teaches that in order to vary the ratio of sample to inert fluid a different size cell for each sample to inert fluid ratio must be used.

A spectrometer comprising processing means for calculating the absorbance or emission of a sample may be characterised in that the processing means is arranged to provide a control signal for application to the sample flow rate varying means to control the flow of sample to cause the calculated absorbance to lie within predetermined limits. Thus by varying the rate of flow of sample while maintaining the total flow rate constant the proportion of sample and diluent can be altered to dilute the sample to bring the measurement within the most sensitive range of the instrument.

The delivery means may comprise a vessel having a converging portion to which the tube is attached, or on which the tube is formed, means for feeding the diluent into the vessel at a constant pressure, and means for feeding the sample into the vessel at an adjustable rate, in which the sample feeding means includes a further tube having a sample delivery end positioned adjacent to and aligned with the first mentioned tube.

This provides a simple arrangement which enables the sample to be entrained as a core within a flow of diluent. The quantity of sample delivered can be made variable while the total flow of sample and diluent through the tube is maintained constant.

The further tube may be movable from a first position in a sample container to said position aligned with the first tube. This allows a quantity of sample to be taken up into the further tube and discharged from the further tube at a controlled rate into the first tube.

A guide may be arranged within the vessel coaxially with the first tube, the guide being present to aid the positioning of the tube within the vessel. This enables an easily repeatable positioning of the sample tube and ensures correct alignment thereof.

An embodiment of the invention will now be described, by way of example, with reference to the accompanying drawings in which:

FIG. 1 shows an atomic absorbtion spectrometer in accordance with the invention including means for diluting a sample to be analysed, FIG. 2 shows on an enlarged scale a portion of the sample and diluent mixing chamber used in the spectrometer of FIG. 1.

Figure 3:
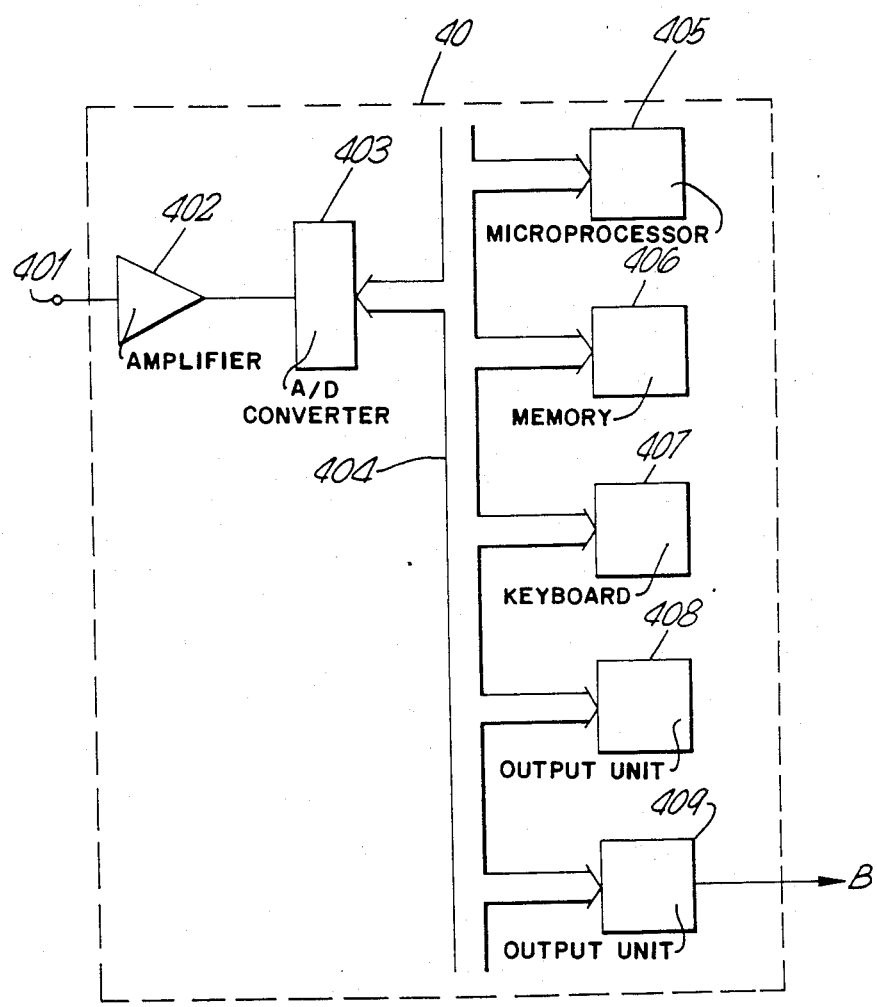
FIG. 3 shows in block schematic form the processing means of the spectrometer of FIG. 1.

The spectrometer shown in FIG. 1 has a mixing vessel 1 in which a sample liquid 12 and a diluent liquid 16 are mixed. The mixing vessel 1 is provided with a conical portion 2 which has a circular outlet opening 3 which leads to a cylindrical section 4 to which a first tube 5 is connected. The outer end of the first tube 5 terminates with an outlet opening 6 in a nebuliser 47. A second tube 10, through which the sample liquid 12 is delivered, is aranged coaxially with the cylindrical section 4 along the axis 9 of symmetry of the conical section of the mixing vessel 1. A supply of oxidising gas, for example air or oxygen, is fed through an inlet 46 of the nebuliser 47. The liquid will be drawn from the tube 5 into a chamber 44 by the flow of oxidising gas due to the Venturi effect. The liquid will be nebulised and to ensure that a consistent droplet size is achieved a spherical bead 48 is located in front of the opening 6. A fuel gas is supplied via an inlet 45 and carries the mist of droplets of sample and diluent through a supply tube 43 to a burner 42. The burner is of elongate form and supports a flame 35 in which the sample is atomised, the burner 42 and flame 35 forming a flame atomiser 7.

The spectrometer further includes a hollow cathode lamp 30 which provides a source of resonance line radiation characteristic of a particular element whose presence in the sample is to be detected. The radiation from the hollow cathode lamp is directed through the flame 35 onto a monochromator 31. The monochromator 31 selects radiation having the wavelength of that emitted by the hollow cathode lamp and passes it to a detector 36, which may be a photomultiplier tube. The output of the detector 36 is passed to a processing circuit 40 which may include a microprocessor. The output of the processing circuit 40 is fed to a display device 41 which may for example comprise a printer, a chart recorder or a video display unit.

The processing and control circuit 40 has an output B which is used to drive a stepping motor which in turn controls the advance of a piston 13 within the syringe 15 which delivers sample liquid through the tube 10 to the mixing chamber 1. The stepping motor advances a threaded rod 60 attached to the piston 13 of the syringe 15 to controllably discharge the sample fluid through the tube 10. The diluent is kept at a constant level 17 in the mixing vessel 1, the level 17 being the same as the level 18 in the vessel 27 which is connected to the vessel 1 by means of a connection 20. The level in the vessel 27, which has an opening 49 to atmosphere, is maintained from a sealed vessel 19 which is inverted and has a tube 22 whose end is dipped in the liquid in the vessel 27. Liquid 16 escapes from the vessel 19 when the level 18 in the vessel 27 drops sufficiently for air to leak through the tube 22 into the vessel 19. This works on the same principle as the well known bird's drinking vessel. Thus a constant flow of liquid through the tube 5 is ensured the flow rate being mainly determined by the Venturi effect of the oxidising gas at the nebuliser. The tube 5 is maintained fully filled by the diluent fluid, the sample fluid being mixed with the diluent fluid. The total amount of sample fluid depends on the rate of advance of the piston 13 in the syringe 15. Thus the sample may vary from a thin thread in the middle of the tube to a column of circular cross section which nearly fills the tube. Consequently a wide range of concentrations of sample can be achieved while ensuring that no sample comes into contact with the walls of the tube 5. Other methods may be used for keeping the level 17 of diluent in the mixing vessel 1 constant. For example float valves or an excess supply and overflow system could be used.

The signal processing and control circuit 40 will include means for calculating the absorbance of the sample and for driving some form of display. It will also include means for controlling the rate of injection of sample into the mixing vessel 1. The circuit 40 may be microprocessor based and may in substance be that described in European Patent Application No. 0086508, and in U.S. patent application Ser. No. 617,069, the contents of which are hereby incorporated by reference.

The tube 10 is movable from the position shown where it is within a guide 50 in the mixing vessel 1 and a position 52 where it is free to discharge into a vessel 53, or it may be positioned 58 with its end in a vessel 59 containing sample liquid 12. In order to deliver a sample into the mixing vessel the tube 10 is inserted into the sample vessel 59 as indicated by reference numeral 58 against the dotted portion in the Figure. The piston 13 in the syringe 15 is withdrawn to aspirate a quantity of the sample 12. The tube 10 is then inserted in the portion 50 of the mixing vessel 1 and lowered until a stop 51 engages with the upper surface of the vessel 1. The tube 10 is then aligned with the tube 5. The piston 14 in the syringe 15 is then advanced at a controlled rate to inject the sample into the tube 5. The rate at which the sample is injected is controlled via the control circuit 40 which drives a stepper motor which in turn drives the piston forward on the threaded shaft 60.

At the completion of the analysis the tube 10 is moved to the position 52 and a valve 56 is opened whereupon a flushing liquid 54 from a vessel 55 is passed through a tube 57 and the syringe 15 and flushes out any remaining sample liquid 12' within the syringe 15 and the pipe 10 into an overflow vessel 53.

The mechanism for moving the sample delivery tube 10 may, for example, be similar to that shown in European Patent Application No. 0015025 and as sold by the Unicam Ltd., under the type no. FAS1. Alternatively the tube 10 may be fixed in position in the mixing vessel 1 and an autosampler of the type sold by Pye Unicam Ltd. as part of the PU9000 series atomic absorption spectrometers could be used. Such an autosampler is described in European Patent Applications Nos. 0103328 and 0103329. Many types of autosampler are available and well known to workers skilled in the art.

FIG. 2 shows the circled area A of FIG. 1 on an enlarged scale and illustrates how the sample liquid is entrained as a central core in a flow of dilvent liquid. The diluent 16 in the converging portion 2 is constrained by the converging portion 2 to flow into the tube with a laminar flow, indicated by the lines 28 and as the tybe 10 is located centrally in the converging portion the same liquid 12 issuing from the tube 10 is surrounded by the diluent 16. Consequently the sample fluid 12 form a converging section 11 from the end of the tube 10 and the cross-section of the thread 29 of sample liquid in the tube 5 will depend on the rate of advance of the pistion 13 in the syringe 15.

FIG. 3 shows in block schematic form the signal processing and control circuit 40. An input 401 receives the signal from the detector 36 and applies it to an amplifier 402 which may be a logarithmic amplifier. The output of the amplifier 402 is fed to an analogue to digital converter 403. A bus 404 connects together the analogue to digital converter 403, a microprocessor 405, a program memory 406, a keyboard 407, an output unit 408 which drives the display unit 41, and an output unit 409 which drives the stepper motor via the output B.

Figure 4:
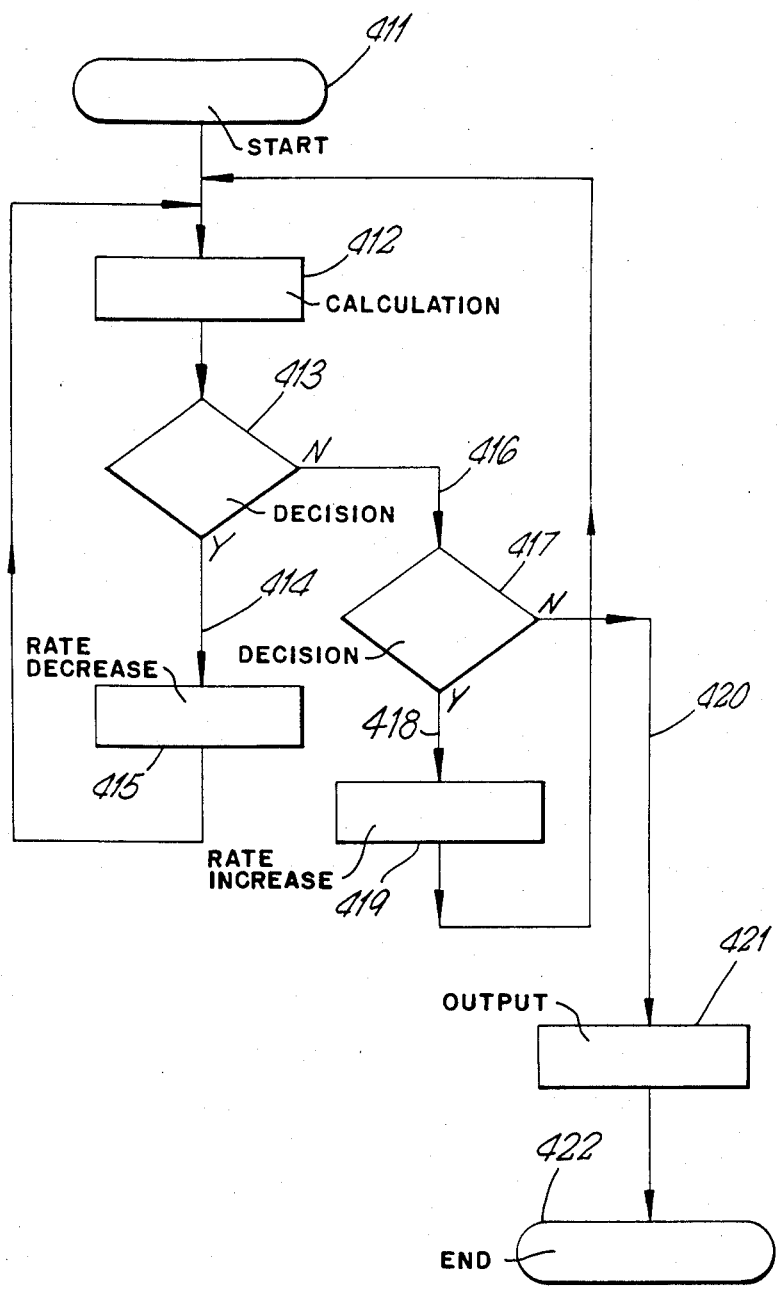
FIG. 4 is a flow diagram showing the operation of the spectrometer shown in FIG. 1.

FIG. 4 shows a flow diagram of the operation of the control unit 40 as far as the driving of the stepper motor is concerned. In FIG. 4 box 411 denotes the start of a sample measurement sequence. Box 412 represents a calculation of a measured absorbance value by means of the unit 40. Box 413 represents a decision as to whether the measured absorbance is greater than a first preset limit. If the absorbance is greater than the first preset limit then path 414 is followed and box 415 represents the action of decreasing the rate at which stepping pulses are supplied to the stepper motor. Thus the quantity of sample relative to that of the diluent will be decreased. When the stepper motor speed has been decreased then the absorbance is again measured and calculated and a decision as to whether or not the absorbance is greater than the first preset limit is again taken. This process is repeated until the absorbance is less than that of the first preset limit. When the absorbance is less than the first preset limit then path 416 is taken and a further decision is taken as to whether the calculated absorbance is less than a second preset limit. This is represented by box 417. If the calculated absorbance is less than the second preset limit then path 418 is followed and box 419 represents an action to increase the rate at which stepping pulses are applied to the stepper motor. Thus the concentration of the sample relative to the diluent is increased and the procedure of measuring and calculating the absorbance is repeated until the absorbance measured is greater than the second preset limit, in which case path 420 is followed and box 421 represents the outputting of the absorbance value to the display unit 41. Box 422 marks the end of the sequence.

The upper limit for absorbance is determined in box 413 and the lower limit for absorbance is determined in box 417. The upper and lower limits are set so that the instrument sensitivity is at its maximum in the range between the two limits. By using the dilution vessel 1 and controlling the rate of advance and withdrawal of the piston 14 in the syringe 15 a continuous range of dilutions can be obtained and hence a continuous range of absorbances can be determined. By using a mixing vessel of the type shown in FIGS. 1 and 2 the problem of cross contamination between successive samples is reduced as the sample liquid does not come into contact with the tube 5 connecting the mixing vessel to the nebuliser. As has been stated earlier, the problem of sample carry over within the nebuliser cloud chamber is not significant due to the scavenging effects of the oxidising and fuel gases.

While the invention has been described with reference to use in an atomic absorption spectrometer it would be equally applicable to an emmission spectrometer or to an atomic fluorescence spectrometer. Depending on the optical arrangement of the spectrometer, the same dilution system could be used to bring the concentration of the sample to a suitable value for the measurement conditions in any of these types of instrument.

What is claimed is:

1. A spectrometer comprising a flame atomiser in the form of a burner, a nebuliser for feeding a sample for analysis entrained in a flow of fuel gas to the burner, a tube for feeding the sample and a diluent to the nebuliser, and means for varying the rate of flow of the sample into the tube while maintaining constant the total flow of sample and diluent, characterised by delivery means for causing the sample and diluent to pass through the tube with laminar flow, the sample being entained as a central core within the flow of diluent.

2. A spectrometer as claimed in claim 1 characterised in that the delivery means comprises a vessel having a converging portion to which the tube is attached, or on which the tube is formed, means for feeding the diluent into the vessel at a constant pressure, and means for feeding the sample into the vessel at an adjustable rate, in which the sample feeding means includes a further tube having a sample delivery end positioned adjacent to and aligned with the first mentioned tube.

3. A spectrometer as claimed in claim 2 characterised in that the further tube is movable from a first position in a sample container to said position aligned with said first tube.

4. A spectrometer as claimed in claim 3 characterised in that a guide is arranged within the vessel, coaxially with the first tube, the guide being present to aid the positioning of the further tube within the vessel.

5. A spectrometer as claimed in claim 1, 2, 3, or 4, characterised by means for maintaining a constant head of diluent above the entrance to the first tube.

6. A spectrometer as claimed in claim 1, 2, 3, or 4, comprising processing means for calculating the absorbance or emission of a sample atomised in the flame, characterised in that the processing means is arranged to provide a control signal for application to the sample flow rate varying means to control the rate of flow of sample to cause the calculated absorbance or emission to lie within predetermined limits.

* * * * *